United States Patent
Kalafer et al.

(10) Patent No.: US 9,314,452 B2
(45) Date of Patent: Apr. 19, 2016

(54) TREATMENT OF AMYOTROPHIC LATERAL SCLEROSIS (ALS) WITH IBUDILAST

(71) Applicant: MediciNova, Inc., La Jolla, CA (US)

(72) Inventors: Michael E. Kalafer, San Diego, CA (US); Kenneth W. Locke, Carlsbad, CA (US); Kazuko Matsuda, Beverly Hills, CA (US); Richard E. Gammans, Edmond, OK (US)

(73) Assignee: MediciNova, Inc., La Jolla, CA (US)

( * ) Notice: Subject to any disclaimer, the term of this patent is extended or adjusted under 35 U.S.C. 154(b) by 199 days.

(21) Appl. No.: 14/188,061

(22) Filed: Feb. 24, 2014

(65) Prior Publication Data

US 2014/0171463 A1 Jun. 19, 2014

Related U.S. Application Data

(63) Continuation of application No. 13/725,627, filed on Dec. 21, 2012, now Pat. No. 9,114,136, which is a continuation of application No. 13/402,702, filed on Feb. 22, 2012, now Pat. No. 8,338,453, which is a continuation of application No. 12/169,042, filed on Jul. 8, 2008, now Pat. No. 8,138,201.

(60) Provisional application No. 60/929,745, filed on Jul. 11, 2007, provisional application No. 61/042,181, filed on Apr. 3, 2008.

(51) Int. Cl.
*A61K 31/437* (2006.01)

(52) U.S. Cl.
CPC .................................. *A61K 31/437* (2013.01)

(58) Field of Classification Search
CPC .................................................. A61K 31/437
USPC ........................................................ 514/300
See application file for complete search history.

(56) References Cited

U.S. PATENT DOCUMENTS

| 6,395,747 | B1 | 5/2002 | Sakoda |
| 2005/0043319 | A1 | 2/2005 | Schweighoffer et al. |
| 2005/0187203 | A1 | 8/2005 | Jost-Price et al. |
| 2006/0160843 | A1 | 7/2006 | Johnson et al. |

FOREIGN PATENT DOCUMENTS

| EP | 1 106 178 A1 | 6/2001 |
| JP | 2004-532809 T | 10/2004 |
| WO | WO-00/09127 A1 | 2/2000 |
| WO | WO-02/45749 A2 | 6/2002 |
| WO | WO-2006/063048 A2 | 6/2006 |
| WO | WO-2007/047978 A2 | 4/2007 |

OTHER PUBLICATIONS

Zoccolella et al. Current and emerging treatments for amyotrophic lateral sclerosis. Neuropsychiatric Disease and Treatment (5) 577-595 (2009).*
Pandya et al. Therapeutic neuroprotective agents for amyotrophic lateral sclerosis. Cell Mol Life Sci. 70 (24): 4729-4745 (2013).*
Yacila et al. Potential Therapeutic Drugs and Methods for the Treatment of Amyotrophic Lateral Sclerosis. Curr Med Chem. 21(31): 3583-3593 (2014).*
Approved Drug Products With Therapeutic Equivalence Evaluations, 29th Edition, U.S. Department of Health and Human Services, Food and Drug Administration Center for Drug Evaluation and Research Office of Pharmaceutical Science Office of Generic Drugs, 2009, 3 pages. (Table of Contents).
Baker et al., "Models of Multiple Sclerosis," Advances in Clinical Neuroscience and Rehabilitation, vol. 6, No. 6, Jan./Feb. 2007, pp. 10-12.
Barkhof et al., "Ibudilast in relapsing-remitting multiple sclerosis," Neurology, Mar. 30, 2010, 74:1033-1040; published at www.neurology.org, 1-8.
Boulton et al., Animal Models of Neurological Diseases, I, Neurodegenerative Diseases, Neuromethods, 21, Humana Press, Totowa, New Jersey, 1992.
English Translation of Second Office Action for CN 200880106623. X, mailed Apr. 28, 2012.
Examination Report mailed Dec. 9, 2010 in European Application No. 08781498.4.
Extended European Search Report issued in EP 12 1961080.0, mailed Jan. 24, 2013.
Feng et al., "Ibudilast, a nonselective phosphodiesterase inhibitor, regulates Th1/Th2 balance and NKT cell subset in multiple sclerosis," Multiple Sclerosis, 2004, 10:494-498.
Fox, "Primary neuroprotection, The Holy Grail of multiple sclerosis therapy," Neurology, vol. 74, pp. 1018-1019 published at www.neurology.org.
Fujimoto et al., "Ibudilast, A Phosphodiesterase Inhibitor, Ameliorates Experimental Autoimmune Encephalomyelitis in Dark August Rats," Journal of Neuroimmunology, vol. 95, pp. 35-42 (1999).
Ganguly, "The Diagnosis of Multiple Sclerosis," Ethics Journal of the American Medical Assosiation, Virtual Mentor, vol. 8, Feb. 2006, pp. 93-96.
Gibson et al., "The Inhibitory Profile of Ibudilast Against the Human Phosphodiesterase Enzyme Family," European Journal of Pharmacology, vol. 538, pp. 39-42 (2006).
Goodman & Gilman's the Pharmacological Basis of Therapeutics, Eleventh Edition, McGraw-Hill Medical Publishing Division, USA, 2006.
Handbook of Pharmaceutical Excipients, Third Edition, Edited by Arthur H. Kibbe, Ph.D., Americal Pharmaceutical Association, Washington, DC, Pharmaceutical Press, London, UK, 2000.

(Continued)

Primary Examiner — Jeffrey S Lundgren
Assistant Examiner — Sara E Townsley
(74) Attorney, Agent, or Firm — Gilberto M. Villacorta; Lydia B. Choi; Foley & Lardner LLP

(57) ABSTRACT

Compositions and methods for treating progressive neurodegenerative diseases, and their associated symptoms by administration of ibudilast (3-isobutyryl-2-isopropylpyrazolo[1,5-a]pyridine).

12 Claims, 3 Drawing Sheets

(56) References Cited

OTHER PUBLICATIONS

Hau et al., Handbook of Laboratory Animal Science, Second Edition, vol. I, Essential Principles and Practices, CRC Press, Boca Raton FL, 2003.
Hau et al., Handbook of Laboratory Animal Science, Second Edition, vol. II, Animal Models, CRC Press, Boca Raton FL, 2003.
Hau et al., Handbook of Laboratory Animal Science, Second Edition, vol. III, Animal Models, CRC Press, Boca Raton, FL, 2003.
Iwasaki et al., "Ibudilast Improved the Memory of Disturbances and Hippocampal Apoptosis in Non-Transgenic Animal Model of Alzheimer's Disease," Society for Neuroscience Abstract Viewer and Itinerary Planner, & 32nd Annual Meeting of the Society for Neuroscience (Nov. 2-7, 2002), vol. 2002.
Jeffery et al., "The Preparation and Characterization of Poly(lactide-co-glycolide) Microparticles. II. The Entrapment of a Model Protein Using a (Water-in-Oil)-in-Water Emulsion Solvent Evaporation Technique", Pharmaceutical Research, vol. 10, No. 3, 1993, pp. 362-368.
Journal of Microencapsulation Microcapsules Liposomes Nanoparticle Smicrocells Microspheres, The Official Journal of the International Microencapsulation Society, vol. 13, No. 6, Nov.-Dec. 1996, Taylor & Francis Publishers.
Kurtzke, "Rating Neurologic Impairment in Multiple Sclerosis: An Expanded Disability Status Scale (EDSS)," Neurology 33, Nov. 1983, pp. 1444-1452.
Ledoux, Animal Models of Movement Disorders, Elsevier Academic Press, Burlington, MA, 2005.
Lehninger, Principles of Biochemistry, Fourth Edition, W.H. Freeman and Company New York.
Levin et al., Animal Models of Cognitive Impairment, Taylor and Francis Group, Boca Raton, FL, 2006.
Mizuno et al., "Neuroprotective role of phosphodiesterase inhibitor ibudilast on neuronal cell death induced by activated microglia," Neuropharmacology, vol. 46, pp. 404-411(2004).
Murashima M. et al., "Inhibitory Effect of Ibudilast (KC-404) on Cyclic Nucleotide Phosphodiesterases," Pharmacology and Therapeutics, Jan. 1998, vol. 26, No. 1, pp. 41-45 {English Translation of Excerpts}.
News-Medical.Net; Pharmaceutical News, Aug. 2, 2005.
Obernolte et al., "The cDNA of a Human lymphocyte cyclic-AMP Phosphodiesterase (PDE IV) Reveals a Multigene Family," Gene 129:239-257 (1993).
Office Action issued in Japanese Patent Application No. 2010-516198, mailed Oct. 30, 2012.
Office Action mailed Dec. 22, 2010 in U.S. Appl. No. 12/169,042.
Physicians' Desk Reference, 52nd Edition, 1998, Published by Medical Economics Co., Inc., Montvale, NJ.
Remington: The Science and Practice of Pharmacy, 20th Edition, Alfonso R. Gennaro Chairman of the Editorial Board and Editor, Lippincott Williams and Wilkins, Baltimore, MD, 2000.
Rile et al., "Potentiation of Ibudilast Inhibition of Platelet Aggregation in the Presence of Endothelial Cells," Thrombosis Research, 102 239-246 (2001).
Search Report and Written Opinion mailed Oct. 14, 2008 in International Application No. PCT/US2008/069417.
Second Office Action for CN200880106623.X, mailed Apr. 28, 2012.
Souness et al., "Possible Role of Cyclic AMP Phosphodiesterases in the Actions of Ibudilast on Eosinophil Thromboxane Generation and Airways Smooth Muscle Tone," British Journal of Pharmacology, 111:1081-1088 (1994).
Sugiyama et al., "SPECT Evaluation of Effect of Cerebral Vasodilator by the Subtraction Method Using Tc-99m HMPAO", Brain and Nerve, vol. 45, No. 2, Feb. 1993, pp. 139-142.
Suzumura et al., "Ibudilast suppresses TNF.alpha. production by glial cells functioning mainly as type III phosphodiesterase inhibitor in NCS," Brain Research, 837:203-212 (1999).
Takuma et al., "Ibudilast attenuates actrocyte apoptsis via cyclic GMP signaling pathway in an in vitro reperfusion model," British Journal of Pharmacology, 133:841-848 (2001).
The Merck Manual of Diagnosis and Therapy, Eighteenth Edition, Published by Merck Research Laboratories, Whitehouse Station NJ, 2006.
The Merck Manual of Medical Information, Second Home Edition, Published by Merck Research Laboratories, Whitehouse, Station NJ, 2003.
The Science and Pharmacy, 1995, Mack Publishing Company, Easton, PA.
Tominaga et al., "Ibudilast protects against neuronal damage induced by glutamate in cultured hippocampal neurons," Clinical and Experimental Pharmacology and Physiology, vol. 23, No. 6-7, 1996, pp. 519-523.
Vukusic et al., "Primary and Secondary Progressive Multiple Sclerosis," Journal of Neurological Sciences, vol. 206, pp. 153-155 (2003).
Yu et al., "Pranlukast, a cysteinyl leukotriene receptor-1 antagonist, protects against chronic ischemic brain injury and inhibits the glial scar formation in mice," Brain Research, 1053, No. 1-2, Aug. 2005, pp. 116-125.
Zhang et al., "Pilot study of minocycline in relapsing-remitting multiple sclerosis," Canadian Journal of Neurological Science, May 2008, 35(2):185-191.
Dhib-Jalbut et al., "Neurodegeneration and neuroprotection in multiple sclerosis and other neurodegenerative diseases," Journal of Neuroimmunology, 2006, p. 198-215.
Office Action issued in corresponding Japanese Application No. 2013-255214 dated Aug. 11, 2015 (with English translation).
Non-Final Office Action issued in U.S. Appl. No. 12/169,042 dated Dec. 22, 2010.
Non-Final Office Action received in U.S. Appl. No. 12/169,042, mailed Oct. 19, 2011.
Notice of Allowance received in U.S. Appl. No. 12/169,042, mailed Jan. 26, 2012.
Notice of Allowance received in U.S. Appl. No. 13/402,702 mailed Aug. 24, 2012.
Official Action received in Canadian Application No. 2,693,697 dated Oct. 16, 2014.
Non-Final Office Action received in U.S. Appl. No. 14/491,939 dated Dec. 18, 2014.
Final Office Action received in U.S. Appl. No. 14/491,939 dated May 7, 2015.
Non-Final Office Action received in U.S. Appl. No. 14/491,939 dated Nov. 16, 2015.

* cited by examiner

TREATMENT OF AMYOTROPHIC LATERAL SCLEROSIS (ALS) WITH IBUDILAST

RELATED APPLICATIONS

This application is a continuation of U.S. patent application Ser. No. 13/725,627, filed Dec. 21, 2012 (now pending), which is a continuation of U.S. patent application Ser. No. 13/402,702, filed 22 Feb. 2012, now U.S. Pat. No. 8,338,453, which is a continuation of U.S. patent application Ser. No. 12/169,042, filed 8 Jul. 2008, now U.S. Pat. No. 8,138,201, which claims the benefit of U.S. Provisional Patent Application Ser. No. 60/929,745, filed 11 Jul. 2007, and U.S. Provisional Patent Application Ser. No. 61/042,181, filed 3 Apr. 2008, the complete disclosures of which are incorporated by reference herein.

FIELD OF THE INVENTION

The present invention relates generally to methods for treating progressive neurodegenerative diseases. In particular, the present invention pertains to methods of treating or preventing progressive neurodegenerative diseases and their associated symptoms by administration of ibudilast (3-isobutyryl-2-isopropylpyrazolo[1,5-a]pyridine).

BACKGROUND OF THE INVENTION

The small molecule ibudilast (3-isobutyryl-2-isopropylpyrazolo[1,5-a]pyridine) is a selective inhibitor of cyclic nucleotide phosphodiesterases (PDEs) 3A, 4, 10A1 and 11A1 (Gibson et al., Eur J Pharmacol 538: 39-42, 2006). Ibudilast also acts as a leukotriene D4 antagonist, an anti-inflammatory, a PAF antagonist, and a vasodilatory agent (Thompson Current Drug Reports). Ibudilast is thought to exert a neuroprotective role in the central nervous system of mammals, presumably via suppression of the activation of glial cells (Mizuno et al., Neuropharmacology 46: 404-411, 2004).

Ibudilast has been widely used in Japan for relieving symptoms associated with ischemic stroke or bronchial asthma. In recent clinical trials, its use in the treatment of multiple sclerosis (MS), an inflammatory disease of the central nervous system, has been explored (News.Medical.Net; Pharmaceutical News, 2 Aug. 2005). As disclosed in this publication, this clinical trial was expected to treat "relapsing-remitting MS," however, no mention is made of progressive multiple sclerosis. In U.S. Pat. No. 6,395,747, ibudilast is disclosed as a treatment for multiple sclerosis, which is generally understood to mean relapsing and remitting multiple sclerosis, not progressive multiple sclerosis. US Patent Application No. 20060160843 discloses ibudilast for the treatment of intermittent and short term pain, however, this is not pain related to a progressive neurodegenerative disease.

While the use of ibudilast for a number of varying indications has been reported to date, to the best of the applicants' knowledge, its use in treating progressive neurodegenerative diseases has heretofore remained largely unexplored.

SUMMARY OF THE INVENTION

The present invention relates to a novel approach to treating progressive neurodegenerative diseases and is based upon the surprising discovery that progressive neurodegenerative diseases can be successfully treated or prevented by administration of ibudilast. Using standard progressive neurodegenerative diseases models, the inventors have discovered that the systemic administration of ibudilast is effective in preventing and/or attenuating, if not eliminating, chronic progressive neurodegenerative diseases, such as that associated with various syndromes.

Accordingly, in one aspect, the invention provides a method of treating a human subject suffering from a progressive neurodegenerative disease by administering to the subject a therapeutically effective amount of ibudilast.

Human subjects suitable to be selected for treatment include those suffering from dementia absent other prominent neurologic signs, Alzheimer's disease, Senile dementia of the Alzheimer type, or Pick's disease (lobar atrophy), neurodegenerative diseases that include syndromes combining progressive dementia with other prominent neurologic abnormalities, progressive neurodegenerative disease mainly afflicting adults and including progressive neurodegenerative forms of Huntington's disease, multiple system atrophy combining dementia with ataxia and/or manifestation of Parkinson's disease, progressive supranuclear palsy (Steele-Richardson-Olszewski), diffuse Lewy body disease, or corticodentatinigral degeneration. Additional subjects can be suffering from progressive neurodegenerative disease that mainly afflicts young adults and children and include Hallervorden-Spatz disease and progressive familial myoclonic epilepsy, progressive neurodegenerative disease that includes syndromes of gradually developing abnormalities of posture and movement, or disease that includes paralysis agitans (Parkinson's disease), striatonigral degeneration, progressive supranuclear palsy, torsion dystonia (torsion spasm; dystonia musculorum deformans), spasmodic torticollis and other restricted dyskinesias, Familial tremor, or Gilles de la Tourette syndrome, syndromes of progressive ataxia, cerebellar degenerations or spinocerebellar degenerations, cerebellar cortical degeneration or olivopontocerebellar atrophy (OPCA), spinocerebellar degenerations including spinocerebellar degenerations (Friedreich's ataxia and related disorders). Other indications include central autonomic nervous system failure (Shy-Drager syndrome), syndromes of muscular weakness and wasting without sensory changes (motor neuron disease), amyotrophic lateral sclerosis (ALS), spinal muscular atrophy, infantile spinal muscular atrophy (Werdnig-Hoffmann), juvenile spinal muscular atrophy (Wohlfart-Kugelberg-Welander), or other forms of familial spinal muscular atrophy, primary lateral sclerosis or hereditary spastic paraplegia, syndromes combining muscular weakness and wasting with sensory changes (progressive neural muscular atrophy; chronic familial polyneuropathies), peroneal muscular atrophy (Charcot-Marie-Tooth), hypertrophic interstitial polyneuropathy (Deferine-Sottas), or miscellaneous forms of chronic progressive neuropathy, progressive neurodegenerative diseases that include syndromes of progressive visual loss. Other indications treatable with the present invention are pigmentary degeneration of the retina (retinitis pigmentosa), or hereditary optic atrophy (Leber's disease), motor neuron disease and the progressive ataxias; sporadic progressive neurodegenerative diseases, multifocal motor neuropathy with conduction block, motor neuropathy with paraproeinemia, motor-predominant peripheral neuropathies, olivopontocerebellar atrophy, Azorean (Machado-Joseph) disease, familial progressive neurodegenerative diseases such as familial amyotrophic lateral sclerosis, spinal muscular atrophies, familial spastic paraparesis, hereditary biochemical disorders, arthrogryposis muliplex congenital, or progressive juvenile bulbar palsy (Fazio-Londe)—Examples of hereditary biochemical disorders are superoxide dismutase deficieny, hexosaminidase A and B deficiency, or androgen receptor mutation (Kennedy's syndrome). Furthermore, progressive neurodegenerative diseases can include viral and prion diseases, such as HTLV-1 associated myelopathy, progressive multifocal leukoencephalopathy, Creutzfeldt-Jakob disease, Gerstmann-Straussler-Scheinker disease, kuru, fatal familial insomnia, or Alper's disease.

In one or more alternative embodiments of the method, ibudilast is administered at a daily dosage amount ranging from about 30 mg to 240 mg daily, or from about 30 mg to 180 mg daily, 60 mg to 120 mg daily, or 20 to 80 mg daily.

The therapeutic dosage amount may be achieved by administration once daily (i.e., in a single dose), twice daily (i.e., in two separate doses), three times daily, or may be administered as multiple doses over a time course of several days, weeks, or even months. Such administering is typically over a duration of time effective to result in a slowing (an inhibition) or diminution (a lessening), and ideally elimination or even reversal, of a progressive neurodegenerative disease. Exemplary durations of treatment include at least about 1 month, from 1 to 3 months, up to about 6 months, up to about 12 months or even longer, such as 24 months or longer. In one particular embodiment, treatment lasts from about 1 week to about 52 weeks.

In a preferred embodiment of the treatment method, the administering is over a duration of time effective to result in elimination of the progressive neurodegenerative disease. Such a time can be a least one year, for at least 20 months or for at least two years.

In a specific embodiment of the invention, a method is described in which an effective amount of ibudilast is administered to patients suffering from a progressive form of relapse remitting multiple sclerosis (RRMS) patients, who are at risk for conversion of their disease to secondary progressive multiple sclerosis (SPMS), whereby the rate of conversion from RRMS to SPMS is decreased by at least approximately half for such patients who are treated daily with an effective amount of ibudilast for a period of at least two years (compared, for example, to untreated patients or to patients treated daily for only one year). Thus, the present method includes a method of administering effective amounts of ibudilast to certain patient populations for at least about two years, at least about three years, at least about four years, or at least about five years and perhaps longer.

In yet another embodiment, ibudilast, when administered either singly or as part of a combination therapy, is administered either systemically or centrally (e.g., by intrathecal administration, i.e., into the cerebrospinal fluid surrounding the spinal cord). Such administration of ibudilast provides a novel mechanism to attenuate progressive neurodegenerative diseases, potentially via suppression of glial activation.

According to yet a further embodiment, ibudilast is administered systemically, e.g. via parenteral, enteral, oral, intravenous, intranasal, sublingual or other systemic routes, to a human, subject for the treatment of progressive neurodegenerative diseases.

In another aspect, the invention provides a composition or combination effective for treating progressive neurodegenerative diseases. The composition comprises a combination of: (i) ibudilast, and (ii) at least one additional agent effective for treating progressive neurodegenerative diseases, where each of the components is either contained in a single composition or dosage form (such as in an admixture), or is present as a discrete or separate entity (e.g., in a kit).

A composition of the invention may optionally include one or more pharmaceutically acceptable excipients.

In yet another aspect, the invention encompasses a kit comprising a combination of medicaments for the treatment of progressive neurodegenerative diseases or a related syndrome, comprising, (i) ibudilast, and (ii) at least one additional agent effective for treating progressive neurodegenerative diseases, for simultaneous, sequential or separate use.

Each of the herein-described features of the invention is meant to apply equally to each and every embodiment as described herein, unless otherwise indicated.

Additional objects, advantages and novel features of the invention will be set forth in the description that follows, and in part, will become apparent to those skilled in the art upon reading the following, or may be learned by practice of the invention.

DETAILED DESCRIPTION OF THE INVENTION

Figure 1:
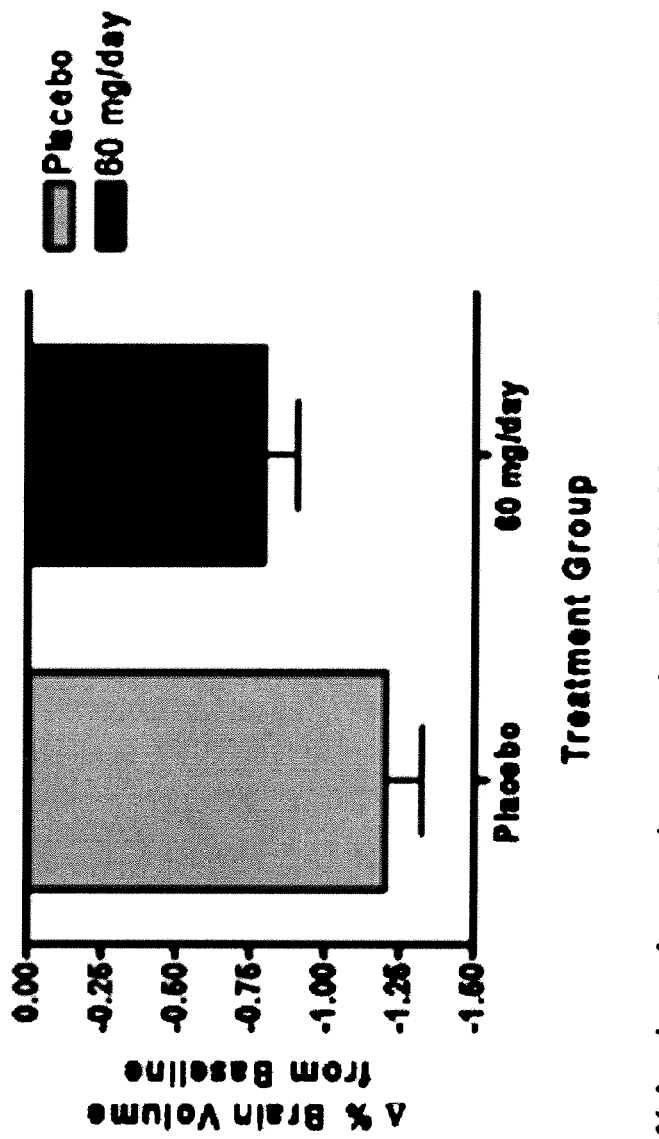
FIG. 1 shows the percent change in brain volume of patients in a Phase II clinical trial. Patients being administered 60 mg a day of ibudilast had an average of 0.79% loss of brain volume, whereas patients being given a placebo had a brain volume loss of 1.2% over a 1-year treatment period. This is a statistically significant result with a p value of 0.0352.
Figure 2:
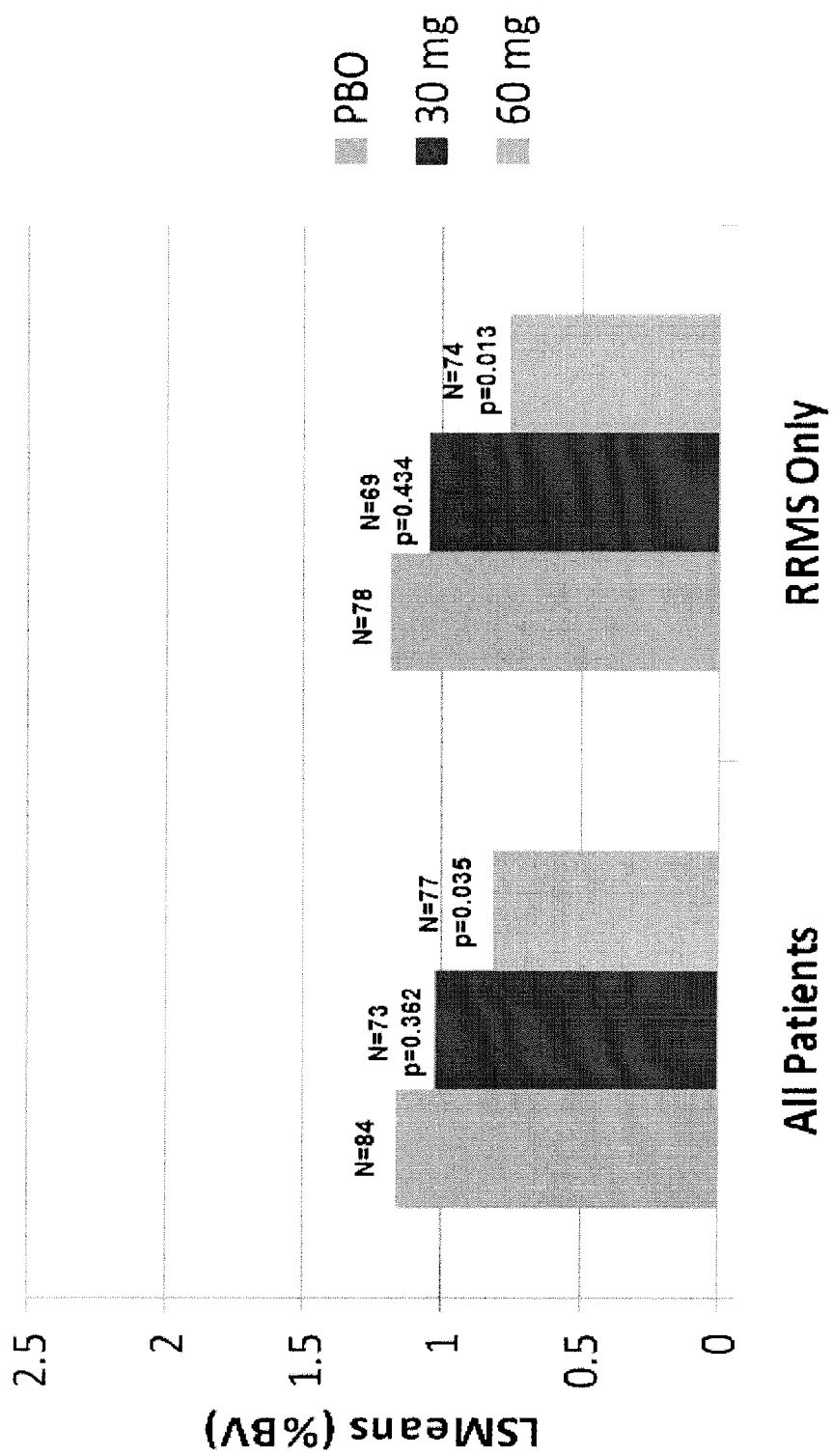
FIG. 2 shows a significant reduction in brain volume loss (p=0.04), as measured by cranial magnetic resonance imaging (MRI) scans, observed after 12 months in MS patients treated with 60 mg per day of MN-166 compared to placebo. A similar effect was observed in the relapsing-remitting patients.
Figure 3:
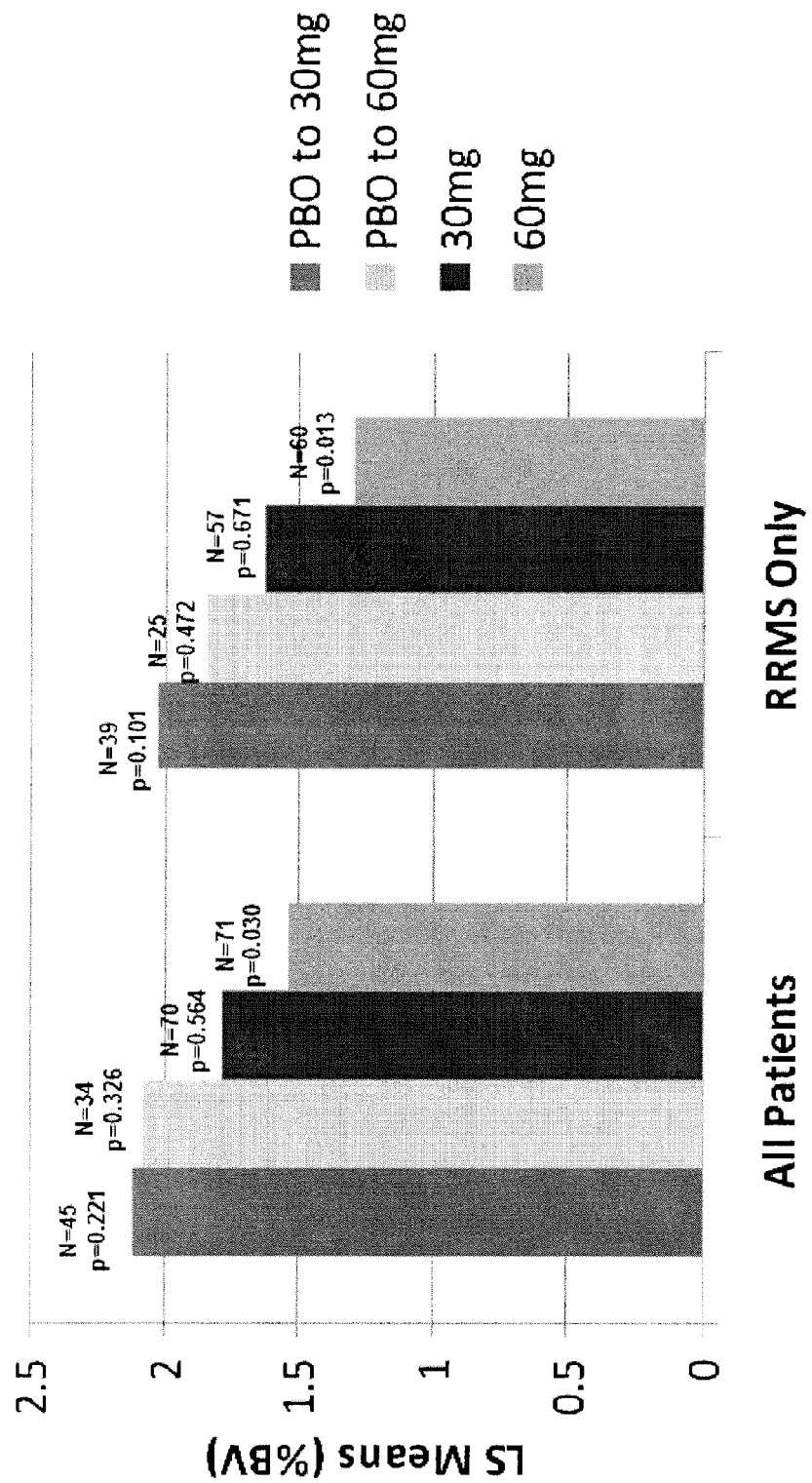
FIG. 3 shows results from a clinical trial in which patients who received placebo during the first 12 months of the trial were randomized to receive either 30 or 60 mg of MN-166 per day (double-blind maintained) during the second 12 months of the trial; patients who received 30 or 60 mg of MN-166 per day during the first 12 months remained on the assigned dose for the second 12 months of the trial.—The results of the trial showed that the significant reduction in brain volume loss (p=0.04), as measured by cranial magnetic resonance imaging (MRI) scans, observed after 12 months in patients treated with 60 mg per day of MN-166 compared to placebo (FIG. 2) was again demonstrated in Year 2 and was significantly less (p=0.030) in patients receiving 60 mg per day of MN-166 for 24 months compared to the other treatment groups (placebo for 12 months, 30 mg MN-166 for 12 months; placebo for 12 months, 60 mg MN-166 for 12 months; 30 mg for 24 months).

The practice of the present invention will employ, unless otherwise indicated, conventional methods of chemistry, biochemistry, and pharmacology, within the skill of the art. Such techniques are explained fully in the literature. See, e.g.; A. L. Lehninger, Biochemistry (Worth Publishers, Inc., current addition); Morrison and Boyd, Organic Chemistry (Allyn and Bacon, Inc., current addition); J. March, Advanced Organic Chemistry (McGraw Hill, current addition); Remington: The Science and Practice of Pharmacy, A. Gennaro, Ed., 20th Ed.; FDA's Orange Book, Goodman & Gilman The Pharmacological Basis of Therapeutics, J. Griffith Hardman, L. L. Limbird, A. Gilman, 11th Ed., 2005, The Merck Manual, 18th edition, 2007, and The Merck Manual of Medical Information 2003.

All publications cited herein, including internet articles, the FDA Orange Book (available on the FDA's website), books, handbooks, journal articles, patents and patent applications, whether supra or infra, are hereby incorporated by reference in their entirety.

Definitions

Before describing the present invention in detail, it is to be understood that this invention is not limited to particular administration modes, patient populations, and the like, as such may vary, as will be apparent from the accompanying description and figures.

It must be noted that, as used in this specification and the intended claims, the singular forms "a," "an," and "the" include plural referents unless the context clearly dictates otherwise. Thus, for example, reference to "a drug" includes a single drug as well as two or more of the same or different drugs, reference to "an optional excipient" refers to a single optional excipient as well as two or more of the same or different optional excipients, and the like.

In describing and claiming the present invention, the following terminology will be used in accordance with the definitions described below.

"Pharmaceutically acceptable excipient or carrier" refers to an excipient that may optionally be included in the compositions of the invention and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including substituted ammonium).

"Active molecule" or "active agent" as described herein includes any agent, drug, compound, composition of matter or mixture which provides some pharmacologic, often beneficial, effect that can be demonstrated in-vivo or in vitro. This includes foods, food supplements, nutrients, nutriceuticals, drugs, vaccines, antibodies, vitamins, and other beneficial agents. As used herein, the terms further include any physiologically or pharmacologically active substance that produces a localized or systemic effect in a patient.

"Substantially" or "essentially" means nearly totally or completely, for instance, 95% or greater of some given quantity.

"Optional" or "optionally" means that the subsequently described circumstance may or may not occur, so that the description includes instances where the circumstance occurs and instances where it does not.

By "progressive neurodegenerative disease" means any neurodegenerative disease that is in the progressive state, or has progressive characteristics and is not solely in the state relapse and or remitting occurrences. A progressive state is a worsening of symptoms over time. Generally, the symptoms worsen at a gradual rate.

Examples of progressive neurodegenerative diseases include Alzheimer's Disease, Parkinsonism and amyotrophic lateral sclerosis.

The term "central nervous system" or "CNS" includes all cells and tissue of the brain and spinal cord of a vertebrate. Thus, the term includes, but is not limited to, neuronal cells, glial cells, astrocytes, cerebrospinal fluid (CSF), interstitial spaces and the like.

"Glial cells" refer to various cells of the CNS also known as microglia, astrocytes, and oligodendrocytes.

The terms "subject", "individual" or "patient" are used interchangeably herein and refer to a vertebrate, preferably a mammal. Mammals include, but are not limited to, murines, rodents, simians, humans, farm animals, sport animals and pets.

The terms "pharmacologically effective amount" or "therapeutically effective amount" of a composition or agent, as provided herein, refer to a nontoxic but sufficient amount of the composition or agent to provide the desired response, such as a reduction or reversal of progressive neurodegenerative diseases. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

The term "about", particularly in reference to a given quantity, is meant to encompass deviations of plus or minus five percent.

"Progressive neurodegenerative disease" means any neurodegenerative disease that is in the progressive state (that is, getting worse compared to a baseline level) or has such progressive characteristics. Thus a progressive state is a worsening of symptoms over time and can be precipitous or gradual. Examples of progressive neurodegenerative diseases include Parkinson's disease, amyotrophic lateral sclerosis, Alzheimer's disease, and progressive forms of multiple sclerosis exclusive of relapse/remitting multiple sclerosis.

There are four recognized types of multiple sclerosis: (1) Relapsing/Remitting Multiple Sclerosis (RR multiple sclerosis), (2) Secondary Progressive Multiple Sclerosis (SP multiple sclerosis), (3) Progressive Relapsing Multiple Sclerosis (PR multiple sclerosis), and (4) Primary Progressive Multiple Sclerosis (PP multiple sclerosis). RR multiple sclerosis is not considered to fall within the scope of the claims, but the other forms of multiple sclerosis, i.e. SP multiple sclerosis, PR multiple sclerosis and PP multiple sclerosis are considered to be one aspect of the present invention. In all types of progressive MS, there is a loss of function over time regardless of relapses.

"Relapsing/Remitting Multiple Sclerosis (RR multiple sclerosis)" is characterized by relapses (also known as exacerbations) during which time new symptoms can appear and old ones resurface or worsen. The relapses are followed by periods of remission, during which time the person fully or partially recovers from the deficits acquired during the relapse. Relapses can last for days, weeks or months and recovery can be slow and gradual or almost instantaneous. The vast majority of people presenting with Multiple Sclerosis are first diagnosed with relapsing/remitting. This is typically when they are in their twenties or thirties, though diagnoses much earlier or later are known. Around twice as many women as men present with this variety.

In "Secondary Progressive Multiple Sclerosis (SP multiple sclerosis)," a person who initially had relapsing-remitting multiple sclerosis begins to develop a gradual deterioration in nerve function, with or without relapses. After a number of years many people who have had relapsing/remitting multiple sclerosis will pass into a secondary progressive phase of the disease. This is characterized by a gradual worsening of the disease between relapses. In the early phases of Secondary Progressive, the person may still experience a few relapses but after a while these merge into a general progression. People often do not return to their prior level of function after a relapse. People with secondary progressive may experience good and bad days or weeks, but, apart from some remission following relapsing episodes, have no real recovery. After 10 years, 50% of people with relapsing/remitting multiple sclerosis will have developed secondary progressive. By 25 to 30 years, that figure will have risen to 90%.

"Progressive Relapsing Multiple Sclerosis (PR multiple sclerosis)" shows clear progression in the level of disability from the time symptoms first begin, but with episodes of clear relapses that may or may not be associated with some recovery following the acute episode. This form of multiple sclerosis follows a progressive course from onset, punctuated by relapses. There is significant recovery immediately following a relapse but between relapses there is a gradual worsening of symptoms.

"Primary Progressive Multiple Sclerosis (PP multiple sclerosis)" is characterized by a gradual progression of the disease from its onset with no remissions or relapses at all. There may be periods of a leveling off of disease activity and, as with secondary progressive, there may be good and bad days or weeks. PP multiple sclerosis differs from Relapsing/Remitting and Secondary Progressive in that onset is typically in the late thirties or early forties, men are as likely women to develop it and initial disease activity is in the spinal cord and not in the brain. Primary Progressive multiple sclerosis often migrates into the brain, but is less likely to damage brain areas than relapsing/remitting or secondary progressive—for example, people with Primary Progressive are less likely to develop cognitive problems.

"Treatment" or "treating" progressive neurodegenerative diseases includes arresting the development or reversing the symptom of a progressive neurodegenerative disease.

"Persistent neuronal or axon damage" includes damage to neurons that is long term or permanent, such as when neurons die and disappear.

"Persistent black hole" is defined as a hypointense lesion. Black holes, or dark areas on a T1 weighted magnetic resonance imaging (MRI) scan, show loss of myelin and loss of axons. As one of skill in the art will appreciate, a T1 weighted scan uses longitudinal relaxation time a short relaxation time (TR) and short echo time (TE) (TR<1000 msec, TE<30 msec).

Ibudilast

The methods of the invention for the treatment of progressive neurodegenerative diseases are based upon administration of the molecule, ibudilast. Ibudilast is a small molecule drug (molecular weight of 230.3) having the structure shown below.

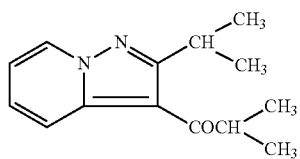

Ibudilast is also found under ChemBank ID 3227, CAS #50847-11-5, and Beilstein Handbook Reference No. 5-24-03-00396. Its molecular formula corresponds to $C_{14}H_{18}N_2O$. Ibudilast is also known by various chemical names including 2-methyl-1-(2-(1-methylethyl) pyrazolo(1,5-a)pyridin-3-yl) 1-propanone; 3-isobutyryl-2-isopropylpyrazolo(1,5-a)pyridine]; and 1-(2-isopropyl-pyrazolo[1,5-a]pyridin-3-yl)-2-methyl-propan-1-one. Other synonyms for ibudilast include Ibudilastum (Latin), BRN 0656579, KC-404, and MN-166. Its brand name is Ketas®. Ibudilast, as referred to herein, is meant to include any and all pharmaceutically acceptable salt forms thereof, prodrug forms (e.g., the corresponding ketal), solvates, and the like, as appropriate for use in its intended formulation for administration.

Ibudilast is a is a selective inhibitor of cyclic nucleotide phosphodiesterases (PDEs) 3A, 4, 10A1 and 11A1 (Gibson et al., Eur J Pharmacol 538: 39-42, 2006), and has also been reported to have leukotriene D4 and PAF antagonistic activities. Its profile appears effectively anti-inflammatory and unique in comparison to other PDE inhibitors and anti-inflammatory agents. PDEs catalyze the hydrolysis of the phosphoester bond on the 3'-carbon to yield the corresponding 5'-nucleotide monophosphate. Thus, they regulate the cellular concentrations of cyclic nucleotides. Since extracellular receptors for many hormones and neurotransmitters utilize cyclic nucleotides as second messengers, the PDEs also regulate cellular responses to these extracellular signals. There are at least eight classes of PDEs: $Ca_2+$/calmodulin-dependent PDEs (PDE1); cGMP-stimulated PDEs (PDE2); cGMP-inhibited PDEs (PDE3); cAMP-specific PDEs (PDE4); cGMP-binding PDEs (PDE5); photoreceptor PDEs (PDE6); high affinity, cAMP-specific PDEs (PDE7); and high affinity cGMP-specific PDEs (PDE9). Ibudilast acts to suppress inflammation via action on inflammatory cells (e.g., glial cells) resulting in the suppression of both pro-inflammatory mediator and neuroactive mediator release. Ibudilast may also suppress the production of pro-inflammatory cytokines (IL-1β, TNF-α) and may enhance the production of the anti-inflammatory cytokines (IL-4, IL-10). References related to the foregoing include the following: Obernolte, R., et al. (1993) "The cDNA of a human lymphocyte cyclic-AMP phosphodiesterase (PDE IV) reveals a multigene family" Gene 129: 239-247; Rile, G., et al. (2001) "Potentiation of ibudilast inhibition of platelet aggregation in the presence of endothelial cells" Thromb. Res. 102: 239-246; Souness, J. E., et al. (1994) "Possible role of cyclic AMP phosphodiesterases in the actions of ibudilast on eosinophil thromboxane generation and airways smooth muscle tone" Br. J. Pharmacol. 111: 1081-1088; Suzumura, A., et al. (1999) "Ibudilast suppresses TNF.alpha. production by glial cells functioning mainly as type III phosphodiesterase inhibitor in CNS" Brain Res. 837: 203-212; Takuma, K., et al. (2001) "Ibudilast attenuates astrocyte apoptosis via cyclic GMP signaling pathway in an in vitro reperfusion model" Br. J. Pharmacol. 133: 841-848.

As stated previously, a reference to any one or more of the herein-described drugs, in particular ibudilast, is meant to encompass, where applicable, any and all enantiomers, mixtures of enantiomers including racemic mixtures, prodrugs, pharmaceutically acceptable salt forms, hydrates (e.g., monohydrates, dihydrates, etc.), solvates, different physical forms (e.g., crystalline solids, amorphous solids), metabolites, and the like.

Method of Administration

As set forth above, the present invention is directed to a method of treating a human subject suffering from a progressive neurodegenerative disease by administering a therapeutically effective dosage of ibudilast. Such administering is effective to decrease the amount of progressive neurodegenerative disease experienced by the subject, i.e., to result in a significant attenuation or even reversal of progressive neurodegenerative disease, as demonstrated in the accompanying Examples. Ibudilast is preferably administered at a daily dosage amount ranging from about 30 mg to 240 mg daily, or from about 30 mg to 180 mg daily, or 60 mg to 120 mg daily.

The method of the invention may, in certain instances, comprise a step of selecting a subject experiencing progressive neurodegenerative diseases prior to administering ibudilast thereto. Such subjects are typically selected from those suffering from: Alzheimer's disease, Senile dementia of the Alzheimer type, or Pick's disease (lobar atrophy), syndromes combining progressive dementia with other prominent neurologic abnormalities, Huntington's disease, multiple system atrophy combining dementia with ataxia and/or manifestation of Parkinson's disease, progressive supranuclear palsy (Steele-Richardson-Olszewski), diffuse Lewy body disease, or corticodentatinigral degeneration, Hallervorden-Spatz disease and progressive familial myoclonic epilepsy, symptoms of gradually developing abnormalities of posture and movement, paralysis agitans (Parkinson's disease), striatonigral degeneration, progressive supranuclear palsy, torsion dystonia (torsion spasm; dystonia musculorum deformans), spasmodic torticollis and other restricted dyskinesias, Familial tremor, or Gilles de la Tourette syndrome, progressive ataxia, cerebellar degenerations or spinocerebellar degenerations, cerebellar cortical degeneration or olivopontocerebellar atrophy (OPCA), spinocerebellar degenerations (Friedreich's ataxia and related disorders), central autonomic nervous system failure (Shy-Drager syndrome), syndromes of muscular weakness and wasting without sensory changes (motor neuron disease), amyotrophic lateral sclerosis (ALS), spinal muscular atrophy, infantile spinal muscular atrophy (Werdnig-Hoffmann), juvenile spinal muscular atrophy (Wohlfart-Kugelberg-Welander), or other forms of familial spinal muscular atrophy, primary lateral sclerosis, or hereditary spastic paraplegia, syndromes combining muscular weakness and wasting with sensory changes (progressive neural muscular atrophy; chronic familial polyneuropathies), peroneal muscular atrophy (Charcot-Marie-Tooth), hypertrophic interstitial polyneuropathy (Deferine-Sottas), or miscellaneous forms of chronic progressive neuropathy, syndromes of progressive visual loss, pigmentary degeneration of the retina (retinitis pigmentosa), or hereditary optic atrophy (Leber's disease), Parkinson's disease and other extrapyramidal disorders, progressive supranuclear palsy (Steele-Richardson-Olszewski syndrome), torsion dystonia (torsion spasm, dystonia musculorum deformans), focal dystonias, Familial tremors, or Gilles de la Tourette syndrome, motor neuron disease and the progressive ataxias, amyotrophic lateral sclerosis, primary lateral sclerosis, multifocal motor neuropathy with conduction block, motor neuropathy with paraproeinemia, motor-predominant peripheral neuropathies, olivopontocerebellar atrophy, Azorean (Machado-Joseph) disease, familial progressive neurodegenerative diseases, familial amyotrophic lateral sclerosis, spinal muscular atrophies, familial spastic paraparesis, hereditary biochemical disorders, arthrogryposis muliplex congenital, or progressive juvenile bulbar palsy (Fazio-Londe), infantile (Werdnig-Hoffman disease), childhood onset, or adolescent (Wohlfart-Kugelberg-Welander disease), familial HTLV-1 myelopathy, isolated FSP, or complicated FSP, superoxide dismutase deficiency, hexosaminidase A and B deficiency, or androgen receptor mutation (Kennedy's syndrome), viral and prion diseases, myelopathy, progressive multifocal leukoencephalopathy, Creutzfeldt-Jakob disease, Gerstmann-Straussler-Scheinker disease, kuru, fatal familial insomnia, or Alper's disease, includes primary progressive or secondary progressive multiple sclerosis, but excludes relapsing, remitting multiple sclerosis, frontotemporal dementia, Wilson's disease, progressive neuropathic pain. In some embodiments of this invention, administering to treat patients with multiple sclerosis is excluded.

Ibudilast may also be administered in combination with an additional agent effective for treating progressive neurodegenerative diseases. In a preferred embodiment, such agent possesses a mechanism of action different from ibudilast. Exemplary agents include cholinesterase inhibitors (e.g., Razadyne® (formerly known as Reminyl®) (galantamine), Exelon® (rivastigmine), Aricept® (donepezil), and Cognex® (tacrine)), N-methyl-D-aspartate (NMDA) inhibitors (e.g., Namenda® (memantine)), levodopa preparations (e.g., levodopa/carbidopa (Sinemet® or Atamet®), levodopa/benserazide (Madopar®), levodopa/carbiopa (Sinemet CR®), levodopa/benserazide (Madopar HBS®), carbidopa/levodopa/entacapone (Stalevo®)), catechol-O-methyl transferase (COMT) inhibitors (e.g., entacapone (Comtan®), tolcapone (Tasmar®)), dopamine agonists (e.g., bromocriptine (Parlodel®), pergolide (Permax®), pramipexole (Mirapex®), ropinirole (Requip®), cabergoline (Dostinex®), apomorphine (Apokyn®), lisuride (Dopergine®)), immunomodulating drugs (e.g., interferon beta-1a (Avonex®, Rebif®), interferon beta-1b (Betaseron®), glatiramer acetate (Copaxone®), natalizumab (Tysabri®)), immunosuppressant/chemotherapy drugs (e.g, mitoxantrone (Novantrone®), azathioprine (Imuran®), cladribine (Leustatin®), cyclophosphamide (Cytoxan®), cyclosporine-A, methotrexate), oral medications for relapsing-remitting multiple sclerosis (fingolimod (FTY720), BG12, laquinimod, teriflunomide), etc.

Preferred methods of delivery of ibudilast-based therapeutic formulations for the treatment of progressive neuropathic diseases include systemic and localized delivery. Such routes of administration include but are not limited to, oral, intra-arterial, intrathecal, intraspinal, intramuscular, intraperitoneal, intranasal, and inhalation routes.

More particularly, an ibudilast-based formulation of the present invention may be administered for therapy by any suitable route, including without limitation, oral, rectal, nasal, topical (including transdermal, aerosol, buccal and sublingual), vaginal, parenteral (including subcutaneous, intravenous, intramuscular, and intradermal), intrathecal, and pulmonary. The preferred route will, of course, vary with the condition and age of the recipient, the particular syndrome being treated, and the specific combination of drugs employed.

An ibudilast composition of the invention, when comprising more than one active agent, may be administered as a single combination composition comprising a combination of ibudilast and at least one additional active agent effective in the treatment of progressive neurodegenerative diseases. In terms of patient compliance and ease of administration, such an approach is preferred, since patients are often adverse to taking multiple pills or dosage forms, often multiple times daily, over the duration of treatment. Alternatively, albeit less preferably, the combination of the invention is administered as separate dosage forms. In instances in which the drugs comprising the therapeutic composition of the invention are administered as separate dosage forms and co-administration is required, ibudilast and each of the additional active agents may be administered simultaneously, sequentially in any order, or separately.

Dosages

Therapeutic amounts can be empirically determined and will vary with the particular condition being treated, the subject, and the efficacy and toxicity of each of the active agents contained in the composition. The actual dose to be administered will vary depending upon the age, weight, and general condition of the subject as well as the severity of the condition being treated, the judgment of the health care professional, and particular combination being administered.

Therapeutically effective amounts can be determined by those skilled in the art, and will be adjusted to the requirements of each particular case. Generally, a therapeutically effective amount of ibudilast will range from a total daily dosage of about 0.1 and 200 mg/day, more preferably, in an amount between 1-240 mg/day, 30-240 mg/day, 1-120 mg/day, 30-120 mg/day, administered as either a single dosage or as multiple dosages. Preferred dosage amounts include dosages greater than about 10 mg BID or TID. That is to say, a preferred dosage amount is greater than about 20 mg/day or greater than 30 mg/day. Dosage amounts may be selected from 30 mg/day, 60 mg/day, 90 mg/day or 120 mg/day or more. Depending upon the dosage amount and precise condition to be treated, administration can be one, two, or three times daily for a time course of one day to several days, weeks, months, and even years, and may even be for the life of the patient. Illustrative dosing regimes will last a period of at least about a week, from about 1-4 weeks, from 1-3 months, from 1-6 months, from 1-52 weeks, from 1-24 months, or longer.

Practically speaking, a unit dose of any given composition of the invention or active agent can be administered in a variety of dosing schedules, depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, every other day, three times weekly, twice weekly, once weekly, twice monthly, once monthly, and so forth.

Approaches for Treatment of Progressive Neurodegenerative Diseases

Ibudilast is a potent suppressor of glial activation (Mizuno et al. (2004) Neuropharmacology 46: 404-411). In a dose-dependent manner, ibudilast has been shown to suppress the production of nitric oxide (NO), reactive oxygen species, interleukin (IL)-1.beta., IL-6, and tumor necrosis factor (TNF) and enhance the production of the inhibitory cytokine, IL-10, along with additional neurotrophic factors including nerve growth factor (NGF), glia-derived neurotrophic factor (GDNF), and neurotrophin (NT)-4 in activated microglia. Thus, ibudilast-mediated-neuroprotection was found to be primarily due to the inhibition of inflammatory mediators and the upregulation of neurotrophic factors.

Ibudilast crosses the blood-brain barrier when administered systemically (Sugiyama et al. (1993) No To Shinkei 45(2):139-42; FIG. 5), thus eliminating the need for more invasive methods of administration in order to access central sites of progressive neurodegenerative diseases.

As shown in Example 1, the inventors of the present invention made the surprising discovery in a human clinical trial that administration of ibudilast can reduce brain volume loss in patients that are suffering from an affliction that causes brain volume to shrink. Without wishing to be bound by a particular theory, the present inventors believe that ibudilast administered in accordance with the present claims will cause a slowing or reversal in the loss of brain volume due to the atrophy and death of neurons in a progressive neurodegenerative disease that causes the brain to shrink; these changes can be tracked in cerebral MR or CT images. This discovery of the slowing or reversal of brain volume shrinkage has significant application in the treatment of progressive neurodegenerative diseases described in this application.

Animal Models

The ability of ibudilast to treat progressive neuropathic diseases can be evaluated by any of the standard progressive neuropathic disease models known in the art. Examples of such models are described in Animal Models of Neurological Disease: Neurodegenerative Diseases (Neuromethods) by Alan A. Boulton, Glen B. Baker, and Roger F. Butterworth (1992); Handbook of Laboratory Animal Science, Second Edition: Volumes I-III (Handbook of Laboratory Animal Science) by Jann Hau (Editor), Jr., Gerald L. Van Hoosier (Editor). (2004); Animal Models of Movement Disorders by Mark LeDoux (Editor), (2005); and Animal Models of Cognitive Impairment (Frontiers in Neuroscience) (2006) by Edward D. Levin (Editor), Jerry J. Buccafusco (Editor).

Formulations of the Invention

In addition to comprising ibudilast, a therapeutic formulation of the invention may optionally contain one or more additional components as described below.

Excipients/Carriers

In addition to ibudilast, the compositions of the invention for treating progressive neurodegenerative diseases may further comprise one or more pharmaceutically acceptable excipients or carriers. Exemplary excipients include, without limitation, polyethylene glycol (PEG), hydrogenated castor oil (HCO), cremophors, carbohydrates, starches (e.g., corn starch), inorganic salts, antimicrobial agents, antioxidants, binders/fillers, surfactants, lubricants (e.g., calcium or magnesium stearate), glidants such as talc, disintegrants, diluents, buffers, acids, bases, film coats, combinations thereof, and the like.

A composition of the invention may include one or more carbohydrates such as a sugar, a derivatized sugar such as an alditol, aldonic acid, an esterified sugar, and/or a sugar polymer. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

Also suitable for use in the compositions of the invention are potato and corn-based starches such as sodium starch glycolate and directly compressible modified starch.

Further representative excipients include inorganic salt or buffers such as citric acid, sodium chloride, potassium chloride, sodium sulfate, potassium nitrate, sodium phosphate monobasic, sodium phosphate dibasic, and combinations thereof.

An ibudilast-containing composition of the invention may also include an antimicrobial agent, e.g., for preventing or deterring microbial growth. Non-limiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

A composition of the invention may also contain one or more antioxidants. Antioxidants are used to prevent oxidation, thereby preventing the deterioration of the drug(s) or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

Additional excipients include surfactants such as polysorbates, e.g., "Tween 20" and "Tween 80," and pluronics such as F68 and F88 (both of which are available from BASF, Mount Olive, N.J.), sorbitan esters, lipids (e.g., phospholipids such as lecithin and other phosphatidylcholines, and phosphatidylethanolamines), fatty acids and fatty esters, steroids such as cholesterol, and chelating agents, such as EDTA, zinc and other such suitable cations.

Further, a composition of the invention may optionally include one or more acids or bases. Non-limiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of any individual excipient in the composition will vary depending on the role of the excipient, the dosage requirements of the active agent components, and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5% to about 98% by weight, more preferably from about 15 to about 95% by weight of the excipient. In general, the amount of excipient present in an ibudilast composition of the invention is selected from the following: at least about 2%, 5%, 10%, 15%, 20%, 25%, 30%, 35%, 40%, 45%, 50%, 55%, 60%, 65%, 70%, 75%, 80%, 85%, 90%, or even 95% by weight.

These foregoing pharmaceutical excipients along with other excipients are described in "Remington: The Science & Practice of Pharmacy", 19th ed., Williams & Williams, (1995), the "Physician's Desk Reference", 52.sup.nd ed., Medical Economics, Montvale, N.J. (1998), and Kibbe, A. H., Handbook of Pharmaceutical Excipients, 3.sup.rd Edition, American Pharmaceutical Association, Washington, D.C., 2000.

Other Actives

A formulation (or kit) in accordance with the invention may contain, in addition to ibudilast, one or more additional active agents effective in treating progressive neurodegenerative diseases. Preferably, the active agent is one that possesses a mechanism of action different from that of ibudilast. Such actives include the combinations for pain listed in US Application No. 20060160843, as well as the active ingredients recognized for treatment for the target diseases. Such active ingredients can be found listed in the FDA's Orange Book, Goodman & Gilman The Pharmacological Basis of Therapeutics, J. Griffith Hardman, L. L. Limbird, A. Gilman, 11th Ed., 2005, The Merck Manual, 18th edition, 2007, and The Merck Manual of Medical Information 2003.

The dosage amounts provided above are meant to be merely guidelines; the precise amount of a secondary active agent to be administered during combination therapy with ibudilast will, of course, be adjusted accordingly and will depend upon factors such as intended patient population, the particular progressive neuropathic disease symptom or condition to be treated, potential synergies between the active agents administered, and the like, and will readily be determined by one skilled in the art based upon the guidance provided herein.

Sustained Delivery Formulations

Preferably, the compositions are formulated in order to improve stability and extend the half-life of ibudilast. For example, ibudilast may be delivered in a sustained-release formulation. Controlled or sustained-release formulations are prepared by incorporating ibudilast into a carrier or vehicle such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. Additionally, ibudilast can be encapsulated, adsorbed to, or associated with, particulate carriers. Examples of particulate carriers include those derived from polymethyl methacrylate polymers, as well as microparticles derived from poly(lactides) and poly(lactide-co-glycolides), known as PLG. See, e.g., Jeffery et al., Pharm. Res. (1993) 10:362-368; and McGee et al., J. Microencap. (1996).

Delivery Forms

The ibudilast compositions described herein encompass all types of formulations, and in particular, those that are suited for systemic or intrathecal administration. Oral dosage forms include tablets, lozenges, capsules, syrups, oral suspensions, emulsions, granules, and pellets. Alternative formulations include aerosols, transdermal patches, gels, creams, ointments, suppositories, powders or lyophilates that can be reconstituted, as well as liquids. Examples of suitable diluents for reconstituting solid compositions, e.g., prior to injection, include bacteriostatic water for injection, dextrose 5% in water, phosphate-buffered saline, Ringer's solution, saline, sterile water, deionized water, and combinations thereof. With respect to liquid pharmaceutical compositions, solutions and suspensions are envisioned. Preferably, an ibudilast composition of the invention is one suited for oral administration.

In turning now to oral delivery formulations, tablets can be made by compression or molding, optionally with one or more accessory ingredients or additives. Compressed tablets are prepared, for example, by compressing in a suitable tabletting machine, the active ingredients in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) and/or surface-active or dispersing agent.

Molded tablets are made, for example, by molding in a suitable tabletting machine, a mixture of powdered compounds moistened with an inert liquid diluent. The tablets may optionally be coated or scored, and may be formulated so as to provide slow or controlled release of the active ingredients, using, for example, hydroxypropylmethyl cellulose in varying proportions to provide the desired release profile. Tablets may optionally be provided with a coating, such as a thin film, sugar coating, or an enteric coating to provide release in parts of the gut other than the stomach. Processes, equipment, and toll manufacturers for tablet and capsule making are well-known in the art.

Formulations for topical administration in the mouth include lozenges comprising the active ingredients, generally in a flavored base such as sucrose and acacia or tragacanth and pastilles comprising the active ingredients in an inert base such as gelatin and glycerin or sucrose and acacia.

A pharmaceutical composition for topical administration may also be formulated as an ointment, cream, suspension, lotion, powder, solution, paste, gel, spray, aerosol or oil.

Alternatively, the formulation may be in the form of a patch (e.g., a transdermal patch) or a dressing such as a bandage or adhesive plaster impregnated with active ingredients and optionally one or more excipients or diluents. Topical formulations may additionally include a compound that enhances absorption or penetration of the ingredients through the skin or other affected areas, such as dimethylsulfoxidem bisabolol, oleic acid, isopropyl myristate, and D-limonene, to name a few.

For emulsions, the oily phase is constituted from known ingredients in a known manner. While this phase may comprise merely an emulsifier (otherwise known as an emulgent), it desirably comprises a mixture of at least one emulsifier with a fat and/or an oil. Preferably, a hydrophilic emulsifier is included together with a lipophilic emulsifier that acts as a stabilizer. Together, the emulsifier(s) with or without stabilizer(s) make up the so-called emulsifying wax, and the wax together with the oil and/or fat make up the so-called emulsifying ointment base which forms the oily dispersed phase of cream formulations. Illustrative emulgents and emulsion stabilizers include Tween 60, Span 80, cetostearyl alcohol, myristyl alcohol, glyceryl monostearate and sodium lauryl sulfate.

Formulations for rectal administration are typically in the form of a suppository with a suitable base comprising, for example, cocoa butter or a salicylate.

Formulations suitable for vaginal administration generally take the form of a suppository, tampon, cream, gel, paste, foam or spray.

Formulations suitable for nasal administration, wherein the carrier is a solid, include a coarse powder having a particle size, for example, in the range of about 20 to about 500 microns. Such a formulation is typically administered by rapid inhalation through the nasal passage, e.g., from a container of the powder held in proximity to the nose. Alternatively, a formulation for nasal delivery may be in the form of a liquid, e.g., a nasal spray or nasal drops.

Aerosolizable formulations for inhalation may be in dry powder form (e.g., suitable for administration by a dry powder inhaler), or, alternatively, may be in liquid form, e.g., for use in a nebulizer. Nebulizers for delivering an aerosolized solution include the AERx™ (Aradigm), the Ultravent® (Mallinkrodt), and the Acorn II® (Marquest Medical Products). A composition of the invention may also be delivered using a pressurized, metered dose inhaler (MDI), e.g., the Ventolin® metered dose inhaler, containing a solution or suspension of a combination of drugs as described herein in a pharmaceutically inert liquid propellant, e.g., a chlorofluorocarbon or fluorocarbon.

Formulations suitable for parenteral administration include aqueous and non-aqueous isotonic sterile solutions suitable for injection, as well as aqueous and non-aqueous sterile suspensions.

Parenteral formulations of the invention are optionally contained in unit-dose or multi-dose sealed containers, for example, ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the types previously described.

A formulation of the invention may also be a sustained release formulation, such that each of the drug components is released or absorbed slowly over time, when compared to a non-sustained release formulation. Sustained release formulations may employ pro-drug forms of the active agent, delayed-release drug delivery systems such as liposomes or polymer matrices, hydrogels, or covalent attachment of a polymer such as polyethylene glycol to the active agent.

In addition to the ingredients particularly mentioned above, the formulations of the invention may optionally include other agents conventional in the pharmaceutical arts and particular type of formulation being employed, for example, for oral administration forms, the composition for oral administration may also include additional agents as sweeteners, thickeners or flavoring agents Kits Also provided herein is a kit containing at least one combination composition of the invention, accompanied by instructions for use For example, in instances in which each of the drugs themselves are administered as individual or separate dosage forms, the kit comprises ibudilast in addition to each of the drugs making up the composition of the invention, along with instructions for use. The drug components may be packaged in any manner suitable for administration, so long as the packaging, when considered along with the instructions for administration, clearly indicates the manner in which each of the drug components is to be administered.

For example, for an illustrative kit comprising ibudilast and gabapentin, the kit may be organized by any appropriate time period, such as by day. As an example, for Day 1, a representative kit may comprise unit dosages of each of ibudilast and gabapentin. If each of the drugs is to be administered twice daily, then the kit may contain, corresponding to Day 1, two rows of unit dosage forms of each of ibudilast and gabapentin, along with instructions for the timing of administration. Alternatively, if one or more of the drugs differs in the timing or quantity of unit dosage form to be administered in comparison to the other drug members of the combination, then such would be reflected in the packaging and instructions. Various embodiments according to the above may be readily envisioned, and would of course depend upon the particular combination of drugs, in addition to ibudilast, employed for treatment, their corresponding dosage forms, recommended dosages, intended patient population, and the like. The packaging may be in any form commonly employed for the packaging of pharmaceuticals, and may utilize any of a number of features such as different colors, wrapping, tamper-resistant packaging, blister paks, dessicants, and the like.

It is to be understood that while the invention has been described in conjunction with preferred specific embodiments, the foregoing description as well as the examples that follow are intended to illustrate and not limit the scope of the invention. Other aspects, advantages and modifications within the scope of the invention will be apparent to those skilled in the art to which the invention pertains.

All references mentioned in this application, including any patents, published patent applications, books, handbooks, journal publications, or the FDA Orange Book are hereby incorporated by reference herein, in their entirety.

EXAMPLES

Example 1

A Phase II placebo-controlled, randomized, double-blind study was conducted using ibudilast in patients with multiple sclerosis. During year 1, patients were treated with 0 mg tid (placebo), 10 mg tid or 20 mg tid of ibudilast; during year 2, patients on placebo were randomized to receive either 10 mg tid or 20 mg tid of ibudilast (patients on 10 mg tid or 20 mg tid during the first year of the study continued on that dose during the second year). A baseline MRI scan was taken two weeks prior to treatment. Brain volume changes were assessed on an annual basis with subsequent MRI scans. MRI scans were performed every two months of the 2-year period to assess changes in T1 and T2 lesions. The results from the first year of the 2-year study are summarized in Table 1 below:

TABLE 1

| Outcome Measure | p-value (pbo vs. 60 mg/day) |
|---|---|
| Annualized relapse rate: | 0.0752 |
| pbo −0.8, 60 mg −0.6 (completers) | 0.1106 |
| pbo −0.9, 60 mg −0.7 (ITT) | |
| Time to first relapse (ITT): | 0.0438 |
| Median for 60 mg >1 year | |
| Median for pbo −244 days | |
| % of subjects exacerbation-free for 1 year (ITT): | 0.033 |
| pbo −41%, 60 mg −56.1% | |
| EDSS (% worsened) (ITT): | 0.1771 |
| pbo −30%, 60 mg −21.4% | |
| IDSS (AUC of change from baseline EDSS): | 0.0365 |
| pbo: −0.05, 60 mg: −0.24 (completers) | 0.1761 |
| pbo: −0.05, 60 mg: −0.16 (ITT) | |
| Disability progression (worsened ≥1.0 on EDSS for 4 mo) (ITT): | 0.334 |
| pbo −8%, 60 mg −4% | |

Example 2

A rat animal model for Alzheimer's disease is administered ibudilast and an improvement in cognitive function is achieved for the group of animals being administered ibudilast, thereby indicating that this model could be effective for the treatment of Alzheimer' disease in humans.

Example 3

An animal model for progressive multiple sclerosis is administered ibudilast and an improvement in functional outcomes is achieved for the group of animals being administered ibudilast, thereby indicating that this model could be effective for the treatment progressive multiple sclerosis.

Example 4

An animal model for Parkinson's disease is administered ibudilast and an improvement in locomotion is achieved for the group of animals being administered ibudilast, thereby indicating that this model could be effective for the treatment Parkinson's disease.

Example 5

Table 2 below show that disability progression (greater than or equal to a 1.0 point increase in the Expanded Disability Status Scale (EDSS) score for 4 consecutive months, see Kurtzke J F (1983). "Rating neurologic impairment in multiple sclerosis: an expanded disability status scale (EDSS)". *Neurology* 33 (11): 1444-52.) was less likely in those patients receiving MN-166 for 24 months than those receiving the drug for 12 months (p=0.026). The p-values at 24 Months were: 2 Year Active (pooling of 30 mg and 60 mg dose groups) vs. Placebo to Active (p=0.0264); 60 mg vs. Placebo to Active (p=0.0516), and 30 mg vs. Placebo to Active (p=0.0832). Loss of brain volume on MRI has been shown to correlate with clinical progression and disability in MS patients. These results are consistent with a potential neuroprotective effect of MN-166 in relapsing MS patients.

TABLE 2

| Disability Progression | | | |
|---|---|---|---|
| Time Period | Placebo to Active (N = 100) | 30 mg (N = 94) | 60 mg (N = 98) |
| 1 Year | 8 (8.0%) | 5 (5.3%) | 4 (4.1%) |
| 2 Years | (to 30 mg/d) (to 60 mg/d) 8/51 (15.7%) 13/49 (26.5%) 21/100 (21%) | 10 (10.6%) p = 0.0832 | 10 (10.2%) p = 0.0516 |
| | | 20/194 (10.4%) p = 0.0264 | |

Example 6

Table 3 shows a double-blind analysis of the MRI data from the first year of treatment of the two-year Phase II clinical trial of MN-166 in multiple sclerosis (MS) was conducted. The analysis showed that MN-166 decreased the formation of black holes (permanent brain lesions believed to indicate the death of nerves in the brain) on magnetic resonance imaging (MRI) in MS patients. Data demonstrated that a 60 mg/day dosing regimen of MN-166 significantly reduced the proportion of new T1 gadolinium-enhancing or new T2 lesions identified at month two of the study that evolved into persistent black holes at month 10 compared to placebo (RR 0.63, p=0.011). Treatment with a 30 mg/day dosing regimen of MN-166 showed a trend toward reduced risk of new lesion evolution to persistent black holes compared to placebo (RR 0.735, p=0.074). Of the 292 patients who received either placebo (n=100), 30 mg/day of MN-166 (n=94) or 60 mg/day of MN-166 (n=98), 72 of the placebo-treated patients, 64 of the patients receiving 30 mg/day of MN-166 and 56 of the patients receiving 60 mg/day of MN-166 had new lesions in month two of the study. The proportions of new lesions evolving to persistent black holes were 0.24, 0.20 and 0.16 in the placebo, 30 mg/day of MN-166 and 60 mg/day of MN-166 treatment groups, respectively. The relative risk (RR) for new lesion evolution to persistent black holes was significantly lower (RR 0.63, p=0.011) in MS patients treated with 60 mg/day of MN-166 and tended to be lower (RR 0.735, p=0.074) in patients treated with 30 mg/day of MN-166 compared to placebo-treated patients.

The study is the result of randomized, double-blind, placebo-controlled analysis of year 1 MRI data with MN-166 administration. MRIs were collected bimonthly during the one year treatment period and were re-evaluated in a double-blind manner for this new analysis. Predefined endpoints for this evaluation were the rate of evolution of new lesions to persistent black holes and remyelinated lesions. The predefined statistical endpoints were at the rate of evolution of new lesions (NL) to persistent black holes (PBH) and remyelinated lesions (RL). New T1 gadolinium-enhancing or new T2 lesions were defined as NL in the first on-study MRI at month 2. Lesions that were hypointense and inactive at month 10 were defined as PBH. Hypointense lesions at month 2 or 4 that were isointense at month 10 were RL. Relative Risk (RR) of NL evolution to PBH and RL per patient was analyzed using a general linear model with the error term from the Poisson distribution.

Overall, the benefits to multiple sclerosis patents of extended (at least about two years) ibudilast administration include, but are not limited to, prolongation of time to relapse (by an average of about 130 days compared with untreated patients), lessened likelihood for sustained disability progression (a decrease in the rate by about 50% compared with patients treated for less than two years), reduction in brain volume loss, and reduction in conversion of acute lesions to persistent black holes.

TABLE 3

Reduction of Persistent Black Hole (PBH) Formation

| Parameter | Treatment Groups | | |
|---|---|---|---|
| | Placebo | 30 mg/day | 60 mg/day |
| # Patients w. New Lesions at Month 2 | 72 | 64 | 56 |
| Mean Proportion of Lesions Evolving to PBH | 0.24 | 0.20 | 0.16 |
| Median Proportion of Lesions Evolving to PBH | 0.17 | 0.08 | 0.04 |
| Relative Risk (for Evolution to PBH) vs. placebo | — | 0.74 | 0.63 |
| p Value | — | 0.074 | 0.011 |

What is claimed is:

1. A method of treating a patient diagnosed with amyotrophic lateral sclerosis (ALS) comprising administering to said patient a therapeutically effective amount of ibudilast or a pharmaceutically acceptable salt thereof ranging between 1-240 mg/day.

2. The method of claim 1 in which the ibudilast or pharmaceutically acceptable salt thereof is administered for at least six months.

3. The method of claim 1 in which the ibudilast or pharmaceutically acceptable salt thereof is administered for at least one year.

4. The method of claim 1 in which the ibudilast or pharmaceutically acceptable salt thereof is administered for at least two years.

5. The method of claim 1 in which the ibudilast or pharmaceutically acceptable salt thereof is administered at least once daily.

6. The method of claim 1 in which the ibudilast or pharmaceutically acceptable salt thereof is administered orally.

7. The method of claim 1 in which the ibudilast or pharmaceutically acceptable salt thereof is administered in an amount of 30 mg to 240 mg daily.

8. The method of claim 1 in which the ibudilast or pharmaceutically acceptable salt thereof is administered in an amount of 30 mg to 120 mg daily.

9. The method of claim 1 in which the ibudilast or pharmaceutically acceptable salt thereof is administered in an amount of 1 mg to 120 mg daily.

10. The method of claim 1 in which the ibudilast or pharmaceutically acceptable salt thereof is administered in a total daily dosage amount selected from the group consisting of 30 mg/day, 60 mg/day, 90 mg/day and 120 mg/day.

11. A method of treating a patient diagnosed with amyotrophic lateral sclerosis (ALS) comprising administering to said patient a therapeutically effective amount of ibudilast or a pharmaceutically acceptable salt thereof ranging between about 0.1 and 200 mg/day.

12. The method of claim 11 in which the ibudilast or pharmaceutically acceptable salt thereof is administered in a total daily dosage amount selected from the group consisting of 30 mg/day, 60 mg/day, 90 mg/day and 120 mg/day.

* * * * *